United States Patent [19]

Caggiani

[11] Patent Number: 5,517,846

[45] Date of Patent: May 21, 1996

[54] ELECTRONIC VACUUM SENSOR

[76] Inventor: Carlos A. Caggiani, 23149 Boca Club Colony, Boca Raton, Fla. 33433

[21] Appl. No.: 198,754

[22] Filed: Feb. 18, 1994

[51] Int. Cl.⁶ .................................................. G01L 27/00
[52] U.S. Cl. ............................ 73/4 R; 73/723; 128/748; 128/673
[58] Field of Search ........................... 73/715, 723, 4 R; 128/748, 673, 675

[56] References Cited

U.S. PATENT DOCUMENTS

| | | |
|---|---|---|
| D. 269,549 | 6/1983 | Gross . |
| 4,141,365 | 2/1979 | Fischell et al. . |
| 4,162,673 | 7/1979 | Patel . |
| 4,175,567 | 11/1979 | Patel . |
| 4,215,699 | 8/1980 | Patel . |
| 4,284,084 | 8/1981 | Binard et al. . |
| 4,349,023 | 9/1982 | Gross . |
| 4,383,532 | 5/1983 | Dickhudt . |
| 4,414,983 | 11/1983 | Evans et al. . |
| 4,485,014 | 11/1984 | Gilroy et al. . |
| 4,512,351 | 4/1985 | Pohndorf . |
| 4,518,383 | 5/1985 | Evans . |
| 4,538,624 | 9/1985 | Tarjan . |
| 4,655,749 | 4/1987 | Fischione ................................ 128/748 |
| 4,721,506 | 1/1988 | Teves . |
| 4,737,146 | 4/1988 | Amaki et al. . |
| 4,808,157 | 2/1989 | Coombs . |
| 4,815,471 | 3/1989 | Stobie ..................................... 128/748 |
| 4,897,080 | 1/1990 | Hamidi . |
| 4,919,653 | 4/1990 | Martinez et al. . |
| 4,940,458 | 7/1990 | Cohn . |
| 4,958,901 | 9/1990 | Coombs . |
| 4,973,305 | 11/1990 | Goltzer . |
| 4,973,312 | 11/1990 | Andrew . |
| 4,985,022 | 1/1991 | Fearnot et al. . |
| 5,024,655 | 6/1991 | Freeman et al. . |
| 5,024,662 | 6/1991 | Menes et al. . |
| 5,084,016 | 1/1992 | Freeman et al. . |
| 5,085,631 | 2/1992 | Leighton . |
| 5,100,390 | 3/1992 | Lubeck et al. . |
| 5,160,323 | 11/1992 | Andrew . |
| 5,163,901 | 11/1992 | Eldor . |
| 5,188,594 | 2/1993 | Zilberstein . |
| 5,205,828 | 4/1993 | Kedem . |
| 5,215,105 | 6/1993 | Kizelshteyn et al. . |
| 5,255,691 | 10/1993 | Otten . |
| 5,257,972 | 11/1993 | Gurmarnik . |
| 5,273,047 | 12/1993 | Tripp et al. ................................ 73/4 R |

Primary Examiner—Richard E. Chilcot, Jr.
Assistant Examiner—Max H. Noori
Attorney, Agent, or Firm—Popham, Haik, Schnobrich & Kaufman, Ltd.

[57] ABSTRACT

A disposable electronic vacuum sensor capable of detecting a relatively low vacuum pressure of about 0.04 to 0.05 inches of water. The sensor includes a body having an LED and an opening at one end, and a channel extending longitudinally into the body from the opening. A power source is housed within the body, and a pair of generally parallel first and second contact blades extend longitudinally through the channel. The first contact blade is attached to the upper surface of the channel and coupled to the LED, the LED is coupled the power source, and the power source is coupled to the second contact blade. The LED is activated by a high-sensitivity vacuum switch comprising the first and second contact blades and a thin flexible diaphragm extending longitudinally through the channel between the second contact blade and the lower surface of the channel. When the opening comes in contact with vacuum pressure, the pressure travels along the diaphragm and raises the diaphragm so that it contacts the second contact blade. The second contact blade is then moved upward by the diaphragm until it contacts the first contact blade, thereby completing a circuit between the LED and the power source and illuminating the LED to indicate vacuum pressure.

19 Claims, 3 Drawing Sheets

ELECTRONIC VACUUM SENSOR

BACKGROUND OF THE INVENTION

1. Field of the Invention

The present invention relates to an electronic vacuum sensor. More specifically, the invention relates to a disposable electronic vacuum sensor capable of detecting low vacuum pressure for use in medical applications, such as administration of epidural anesthesia.

2. Related Art

A number of medical procedures involve catheterization of patients, such as administration of anesthesia either before or during a medical procedure. Often, the anesthesia must be administered either continuously or at regular intervals to maintain the effects of the anesthesia during an extended medical procedure.

For administration of epidural anesthesia, it is necessary to accurately locate a patient's epidural space by inserting a needle having a special rounded, oval point, such as an epidural needle (also referred to as a Tuohy or a Hostead point needle) between two of the patient's vertebrae, through ligamentum flavum (the tough ligament holding the spine together), and into the epidural space. Once the epidural space is located, a catheter can be inserted through a needle into the epidural space for anesthesia administration. Two methods are currently used to locate the epidural spacer the "hanging drop" method and the "loss of resistance" method.

According to the hanging drop method, a small amount of sterile local anesthesia solution is placed in a needle hub. The solution clings to the hub as the needle is advanced into the patient's spine. When the point of the needle enters the epidural space, the drop of anesthesia is sucked into the needle by a vacuum existing or forming in the epidural space. Thus, the person administering the anesthesia, such as an anesthesiologist, stops moving the needle forward when the drop disappears into the needle.

Under the loss of resistance method, a glass 5 or 10 ml syringe containing either air or a sterile solution is attached to a needle. The anesthesiologist pushes the plunger of the syringe while the needle is being inserted into the patient to determine whether there is any resistance ("bounce"). When there is resistance, the syringe will hold the air or solution, indicating that the point of the needle is still in the ligamentum flavum. When there is no longer any resistance and the anesthesiologist is able to move the plunger forward, the needle is in the epidural space. Thus, the anesthesiologist advances the needle and syringe into the patient's spine until there is a loss of resistance, indicating that the point of the needle has entered the epidural space and the contents of the syringe have emptied into the epidural space.

To insert the needle into the epidural space according to these methods, a great amount of pressure must be applied to the needle to penetrate the tough ligamentum flavum. When applying such pressure, the anesthesiologist may lose feeling of the penetration rate and push the needle beyond the epidural space before detecting either movement of the drop of anesthesia into the needle or a loss of resistance, thereby puncturing a hole in the arachnoid membrane and causing leakage of central spinal fluid (CSF) from the spinal fluid space. Loss of CSF may cause the patient to have severe headaches (often called "spinal headache"). Also, puncture of the arachnoid membrane may result in infection of the spinal cord or meningitis.

Therefore, it is desirable to provide a sensitive device and method for detecting a relatively small vacuum pressure, so that the epidural space can be safely and easily located. It is also desirable to provide a disposable, inexpensive vacuum sensor shaped so that it is easily handled and gripped during use.

SUMMARY OF THE INVENTION

The present invention provides a disposable electronic vacuum sensor for detecting a relatively low vacuum pressure, such as the vacuum pressure located or formed in the epidural space of a patient's spinal cord.

The inventive device includes a disposable body having proximal and distal ends. An LED and a vacuum intake port or opening are located at the distal end of the body. Hollow locking means for engaging a needle hub, such as a luer taper lock, is connected to the body at the opening to connect a needle to the opening. A channel extends longitudinally along the body's axis from the opening at the distal end of the body to a point inset from the distal end of the body.

First and second batteries coupled to each other are housed within the body. The first battery is coupled to the LED. A first linear adjustable contact blade is attached to the inner wall of the channel so that it extends longitudinally through the channel and is coupled to the LED to provide power to it. A second linear contact blade extends longitudinally through the channel so that it is generally parallel to and below the first contact blade and is coupled to the second battery. A thin, flexible diaphragm is stretched along the length of the channel between the second contact blade and the lower surface of the channel.

The device can be attached to the hub of a needle, such as an epidural needle, by the locking means. When the needle enters the epidural space, any small amount of vacuum pressure formed or located within the space is translated through the opening and along the diaphragm, moving the diaphragm upward so that it engages the second contact blade. The second contact blade is then moved upward by the diaphragm and contacts the first adjustable contact blade, thereby completing the circuit between the batteries and the LED and illuminating the LED to indicate that the needle has entered the epidural space.

A calibration screw extending vertically through the top surface of the body at the body's distal end and attached to the first contact blade is provided to adjust the vacuum sensitivity of the device. To adjust the device so that it can detect a relatively small vacuum pressure of about 0.04 to 0.05 inches of water, the screw is rotated in a first direction around its axis to move the first adjustable contact blade toward the second contact blade. To adjust the device so that it is less sensitive and only detects a larger vacuum pressure, the screw is rotated in a second direction around its axis opposite the first direction to move the first adjustable contact blade away from the second contact blade.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which.

DETAILED DESCRIPTION OF THE PREFERRED EMBODIMENTS

Figure 1A:
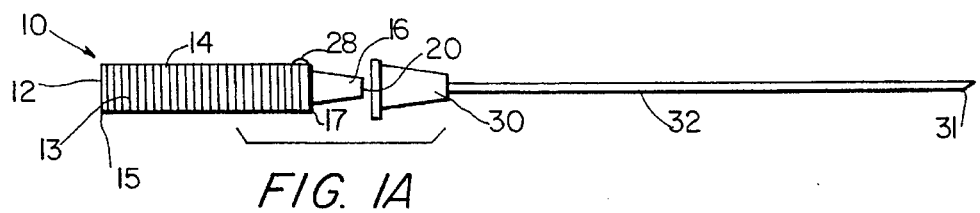
FIG. 1A illustrates an exploded elevational view of the device and a needle.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

Referring to FIG. 1A, the present invention provides a sensor device 10 including a disposable body 12 having proximal and distal ends 15, 17, a vacuum intake port or opening 20 located at its distal end 17, and hollow locking means 16 for engaging a needle hub connected to body 12 over opening 20. Preferably, hollow locking means 16 is a luer taper lock.

Figure 1B:
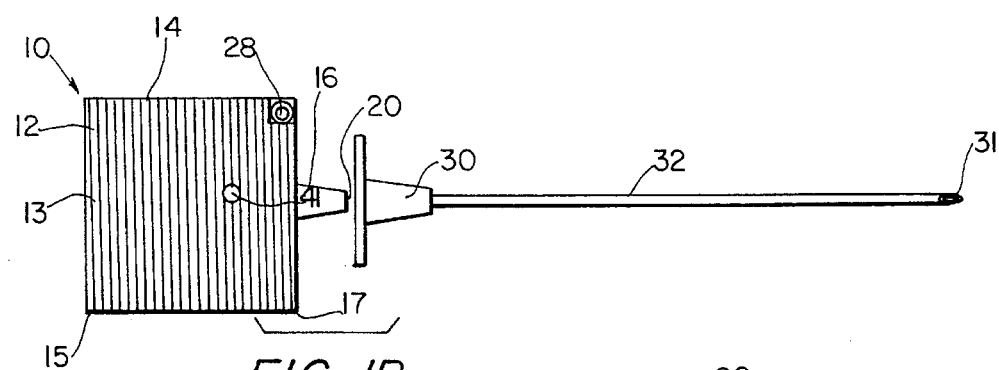
FIG. 1B illustrates an exploded plan view of the device of FIG. 1A.

As shown in FIG. 1B, body 12 can be square. Preferably, body 12 is made of plastic or a similar material and has a ribbed, or otherwise textured, non-slip outer surface 13 for easy handling and gripping of device 10 during use.

Figure 3A:
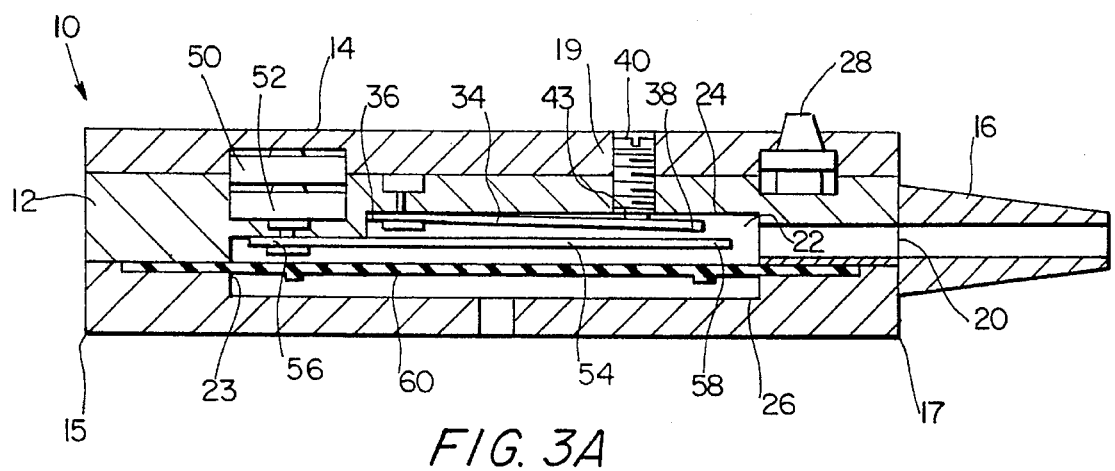
FIG. 3A illustrates a cross-sectional view of the device.

As shown in FIG. 3A, a channel 22 having upper and lower surfaces 24, 26 extends longitudinally through body 12 from opening 20 to a point inset from the proximal end 15 of body 12. A light, preferably an LED 28, is located on the top surface 14 of body 12 at its second end 17 and extends upwardly therefrom. In a preferred embodiment, LED 28 is a 2.1 V, 20 mA LED.

Hollow locking means 16 is configured to engage hub 30 of a needle 32, such as an epidural needle, so that needle 32 can be securely attached to device 10.

Figure 3B:
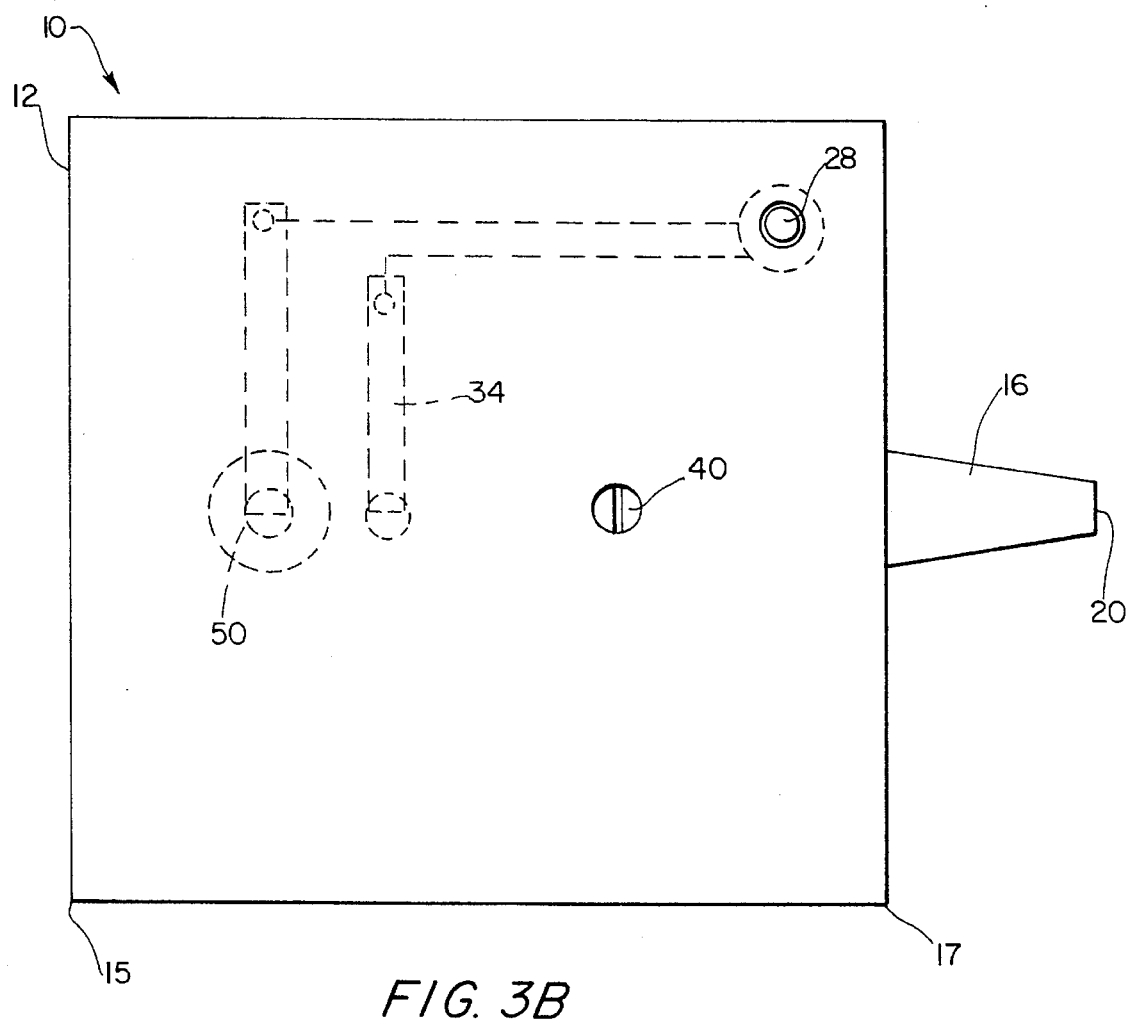
FIG. 3B illustrates a top view of the device shaped according to the alternate embodiment shown in FIG. 1B.

Referring now to FIGS. 3A and 3B, a power source, such as first and second miniature batteries 50, 52, is housed within body 12 at the end 23 of channel 22.

LED 28 is activated by a high-sensitivity vacuum switch comprising first and second linear contact blades 34, 54 and a diaphragm 60.

First adjustable linear contact blade 34 has first and second ends 36, 38 and extends longitudinally through channel 22 and is connected at its first end 36 to upper surface 24 of channel 22. First contact blade 34 is coupled to LED 28, which in turn is coupled to first battery 50, and first battery 50 is coupled to the second battery 52. A calibration screw 40, protected by a removable cover 41 (FIG. 1B) extends through the upper wall 19 of body 12. Its inner end 43 bears against first contact blade 34 near its second end 38 for adjusting its lateral position, and thus the vacuum pressure sensitivity of device 10, as discussed in detail below.

Second linear contact blade 54 has first and second ends 56, 58 and extends longitudinally through channel 22 below and spaced from first contact blade 34. Second contact blade 54 is coupled at its first end 56 to second battery 52. First and second contact blades 34, 54 are formed of a conductive material, preferably metal.

Thin, flexible diaphragm 60 extends longitudinally through channel 22 between second contact blade 54 and lower surface 26 of channel 22. Preferably, diaphragm 60 is made of polytetrafluoroethylene or a similar material capable of being lifted upward bye relatively small vacuum pressure, e.g. 0.04 to 0.05 inches of water, as discussed in detail below.

Figure 2:
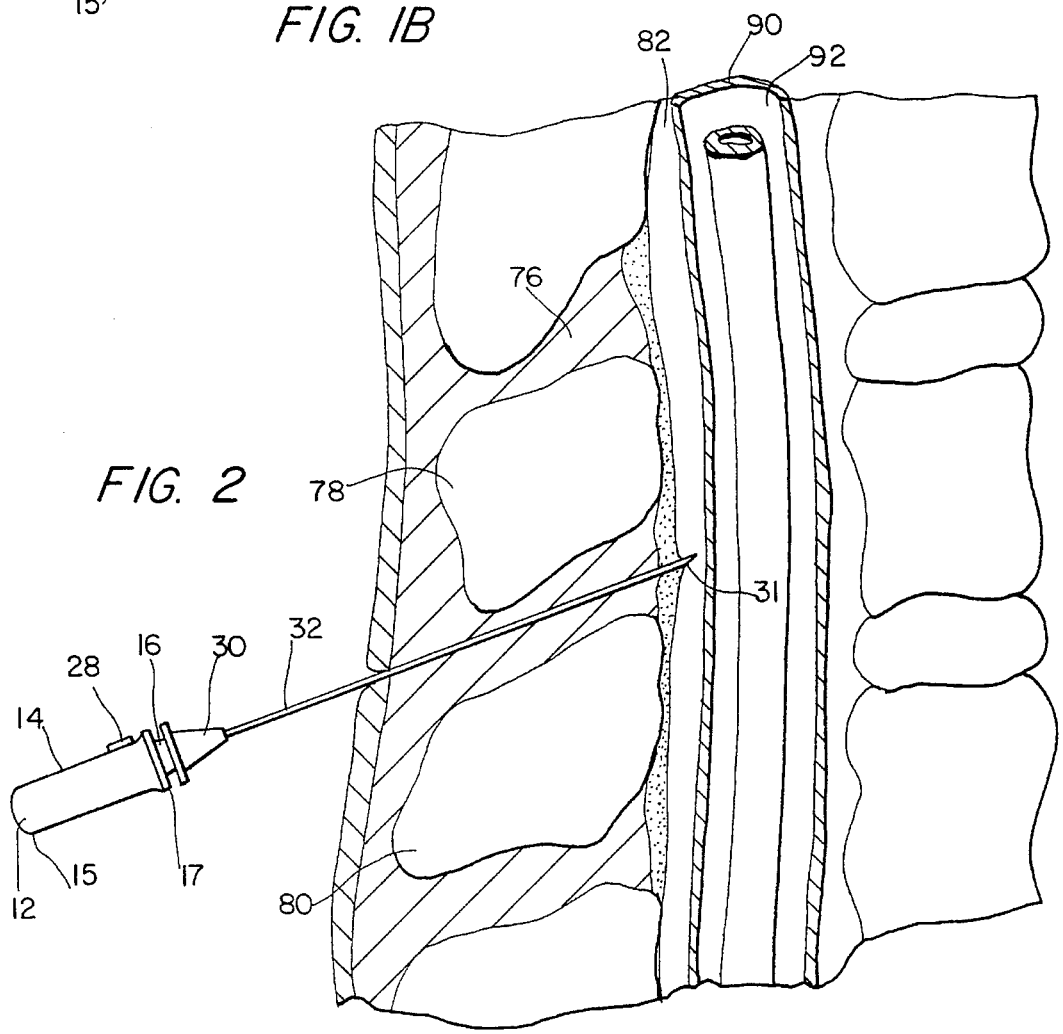
FIG. 2 illustrates a cross-sectional view of a spine with a needle attached to the device and inserted into the epidural space.

Referring now to FIG. 2, the invention further provides a method for detecting a relatively small vacuum pressure, for example in an epidural space, using device 10 in combination with needle 32. First, needle 32 is inserted into a patient, then device 10 is attached to needle 32 before needle 32 reaches the epidural space 82. Device 10 is attached to needle 32 by engaging locking means 16 with hub 30 of needle 32 so that there is a continuous channel extending from point 31 of needle 32 through needle 32, locking means 16, opening 20, and channel 22.

Grasping body 12, needle 52 is inserted further through the patient's ligamentum flavium (interspinous ligament) 76 between two vertebrae 78, 80, and into the epidural space 82. When point 31 of needle 32 enters epidural space 82, vacuum pressure from epidural space 82 is translated through needle 32 and opening 20 and along diaphragm 60, moving diaphragm 60 upward so that it engages second contact blade 54 and moves second contact blade 54 upward. This causes second contact blade 54 to contact first contact blade 34 and complete the circuit between first and second batteries 50, 52 and LED 28, thereby illuminating LED 28 to indicate that needle 32 has entered epidural space 82.

If the arachnoid membrane 90 is accidentally punctured by needle 32, the vacuum pressure will decrease, interrupting the circuit between LED 28 and batteries 50, 52 and causing LED 28 to be turned off. If device 10 is then moved backwards until point 31 of needle 32 is again located within the epidural space 82, the vacuum pressure in epidural space 82 is again detected by device 10 and LED 28 is illuminated to indicate that point 31 of needle 32 has reentered epidural space 82, as described above.

The sensitivity of device 10 can be adjusted by rotating calibration screw 40 in a first direction around its axis to move first contact blade 34 closer to second contact blade 54, thereby enabling device 10 to detect a smaller vacuum pressure. To adjust device 10 so that it is less sensitive and detects only a greater vacuum pressure, calibration screw 40 is rotated in a second direction around its axis opposite the first direction to move first contact blade 34 away from second contact blade 54. Preferably, device 10 is calibrated so that it can detect a vacuum pressure of about 0.04 to 0.05 inches of water, and most preferably about 0.04 inches of water.

Since device 10 is able to detect a relatively small vacuum of about 0.04 inches of water, it is particularly useful in combination with an epidural needle for administering epidural anesthesia or other medical applications. The sensitivity of device 10 allows detection of the vacuum pressure in epidural space 82 by needle 32, indicated by illumination of LED 28, before needle 32 is pushed through the dura and arachnoid membranes 90 and into the subarachnoid (spinal fluid) space 92, thereby avoiding the problems and risks of prior art devices.

Figure 4:
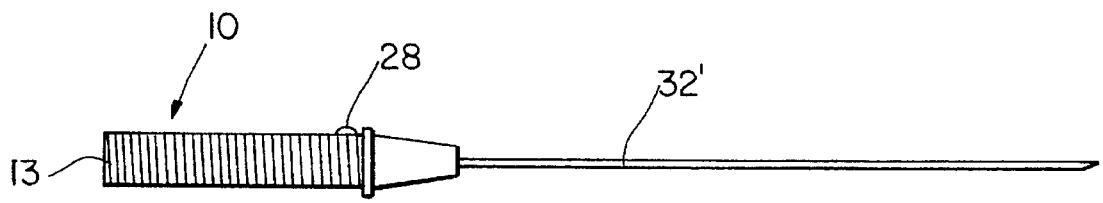
FIG. 4 illustrates an alternate embodiment of the device.
Figure 5:
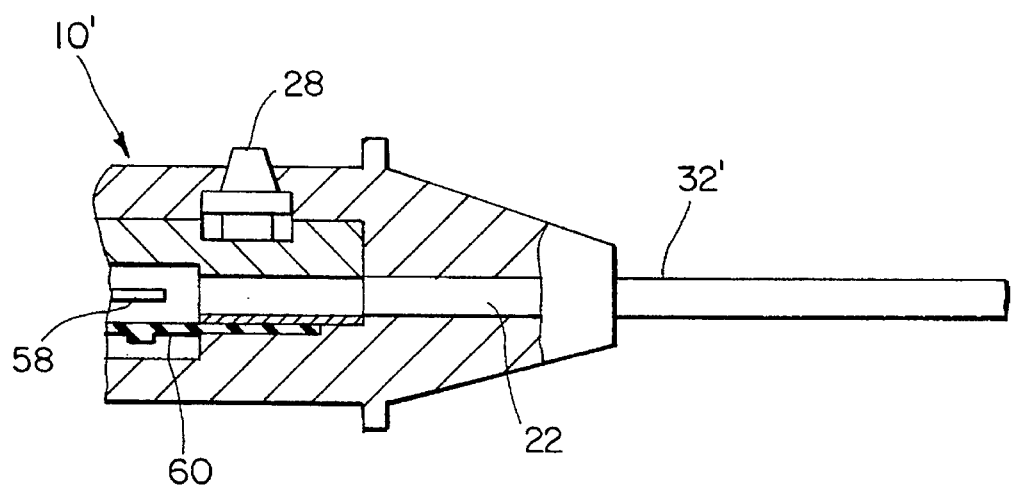
FIG. 5 illustrates a cross-sectional view of the alternate embodiment of the device.

In an alternate embodiment, needle 32' can be attached to or part of device 10' so that needle 32' and device 10' are formed as one piece, as shown in FIGS. 4 and 5.

Modifications and variations of the above-described embodiments of the present invention are possible, as appreciated by those skilled in the art in light of the above teachings. For example, the size and configuration of body 12 can be varied, as can the size, configuration, and location of the components of device 10, such as LED 28 and calibration screw 40.

It is therefore to be understood that, within the scope of the appended claims and their equivalents, the invention may be practiced otherwise than as specifically described.

What is claimed is:

1. An electric sensor device for detecting vacuum pressure comprising:

an elongated body having an opening at one end;

a channel extending longitudinally from the opening into the body, the channel having an upper surface and a lower surface;

a light attached to the body;

first and second batteries coupled to each other and housed within the body, the first battery being coupled to the light;

first and second generally parallel elongated contact members extending longitudinally through the channel, the first contact member being attached to the upper surface of the channel and coupled to the light, and the second contact member being coupled to the second battery; and a diaphragm extending longitudinally through the channel between the second contact member and the lower surface of the channel;

wherein when the opening comes in contact with vacuum pressure, the vacuum pressure is translated through the channel and along the diaphragm, thereby moving the diaphragm upward so it engages the second contact member and moves the second contact member upward to contact the first contact member, thereby completing a circuit between the light and the batteries to illuminate the light, thereby detecting the vacuum pressure.

2. The device of claim 1, wherein the device is capable of detecting a vacuum pressure of about 0.04 to 0.05 inches of water.

3. The device of claim 1, further comprising hollow looking means for attaching a needle to the body, the locking means being connected to the body at the opening.

4. The device of claim 3, wherein the locking means comprises a luer taper lock.

5. The device of claim 1, further comprising a needle attached to the body at the opening.

6. The device of claim 1, further comprising a calibration screw extending vertically through the body and attached to the first contact plate, wherein the sensitivity of the device can be adjusted either by rotating the calibration screw in a first direction around its axis to move the first contact plate closer to the second contact plate so that the device will detect a relatively small vacuum pressure, or by rotating the calibration screw in a second direction around its axis opposite the first direction to move the first contact plate away from the second contact plate so that the device will detect a relatively greater vacuum pressure.

7. The device of claim 1, wherein the body has a textured outer surface.

8. The device of claim 1, wherein the diaphragm is made of polytetrafluoroethylene.

9. The device of claim 1, wherein the body is disposable.

10. An electric sensor device for detecting vacuum pressure comprising:

a body having an opening at one end;

a channel extending longitudinally from the opening into the body, the channel having an upper surface and a lower surfaces a light attached to the body;

a power source housed within the body and coupled to the light;

first and second generally parallel elongated contact members extending longitudinally through the channel, the first contact member being coupled to the light, and the second contact member being coupled to the power source and being movable between a first position spaced from the first contact member and a second position at least partially contacting the first contact members; and a diaphragm extending longitudinally through the channel generally parallel to the second contact member, said diaphragm being movable by vacuum pressure from a first position spaced from the second contact member to a second position at least partially pressing the second contact member and moves the second contact member into contact with the first contact member, thereby completing a circuit between the light and the power source to illuminate the light and indicate vacuum pressure.

11. The device of claim 10, wherein the diaphragm is movable by a vacuum pressure of about 0.04 to 0.05 inches of water.

12. The device of claim 10, further comprising hollow locking means for attaching a needle to the body, the locking means being connected to the body at the opening.

13. The device of claim 12, wherein the locking means comprises a luer taper lock.

14. The device of claim 10, further comprising a needle attached to the body at the opening.

15. The device of claim 10, further comprising a calibration screw extending vertically through the body and bearing against the first contact plate, the calibration screw being rotatable in a first direction around its axis to move the first contact plate closer to the second contact plate and rotatable in a second direction around its axis opposite the first direction to move the first contact plate away from the second contact plate.

16. The device of claim 10, wherein the diaphragm is made of polytetrafluoroethylene.

17. An electric sensor device for detecting vacuum pressure comprising:

a body having an opening at one end;

a channel extending longitudinally from the opening into the body;

a light attached to the body;

a power source housed within the body and coupled to the light; and a high-sensitivity vacuum switch positioned in the channel, the switch activating the light in the presence of a vacuum pressure in the channel.

18. The device of claim 17, further comprising a needle attached to the body at the opening.

19. A method for locating a patient's epidural space with a needle, comprising the steps of:

(a) providing an electric sensor device for detecting vacuum pressure comprising:

a body having an opening at one end;

a channel extending longitudinally from the opening into the body;

a light attached to the body;

a power source housed within the body and coupled to the light; and a high-sensitivity vacuum switch positioned in the channel, the switch activating the light in the presence of a vacuum pressure in the channel;

(b) inserting a needle into the patient's spine;

(c) connecting the device to the needle at the opening; and (d) continuing to insert the needle into the patient's spine until the light becomes illuminated, thereby locating the patient's epidural space.

* * * * *